United States Patent [19]

Nagai et al.

[11] Patent Number: 4,716,240

[45] Date of Patent: Dec. 29, 1987

[54] 1,2-DICHLORO-1,2,2-TRIMETHYL-1-PHENYLDISILANE AND METHOD FOR PRODUCING THE SAME

[75] Inventors: Yoichiro Nagai, Yamato; Hamao Watanabe; Yoshinori Akutsu, both of Kiryu, all of Japan

[73] Assignee: Yuki Gosei Kogyo Co., Ltd., Tokyo, Japan

[21] Appl. No.: 11,964

[22] Filed: Feb. 6, 1987

[30] Foreign Application Priority Data

Feb. 19, 1986 [JP] Japan ................................. 61-32808
Feb. 19, 1986 [JP] Japan ................................. 61-32809

[51] Int. Cl.$^4$ ............................ C07F 7/08; C07F 7/12
[52] U.S. Cl. .................................................... 556/430
[58] Field of Search ........................................ 556/430

[56] References Cited

U.S. PATENT DOCUMENTS 4,266,068  5/1981  Allain et al. ......................... 556/430
4,667,046  5/1987  Frey et al. ........................... 556/430

FOREIGN PATENT DOCUMENTS 59-78196  4/1984  Japan ................................. 556/430
0721443  3/1980  U.S.S.R. ............................ 556/430

OTHER PUBLICATIONS

Gilman et al., "J. of Organomet. Chem.", 6, 1966, pp. 665–668.
Gilman et al., "J. of Organomet. Chem.", 5, 1966, pp. 201–202.

*Primary Examiner*—Paul F. Shaver
*Attorney, Agent, or Firm*—Flynn, Thiel, Boutell & Tanis

[57] ABSTRACT

This invention relates to 1,2-dichloro-1,2,2-trimethyl-1-phenyldisilane expressed by the chemical formula (II),$Cl(CH_3)_2SiSi(CH_3)(C_6H_5)Cl$.

This invention further relates to a method for producing 1,2-dichloro-1,2,2-trimethyl-1-phenyldisilane by reacting phenyl lithium with 1,1,2-trichloro-1,2,2-trimethyldisilane expressed by the chemical formula (III),$Cl(CH_3)_2SiSi(CH_3)Cl_2$.

This invention still further relates to a method for producing 1,2-dichloro-1,2,2-trimethyl-1-phenyldisilane by reacting 1,1,2-trichloro-1,2,2-trimethyldisilane with phenylmagnesium halide expressed by the general formula (IV), $C_6H_5MgX$ (X=halogen atom) in the presence of a cobalt catalyst.

11 Claims, No Drawings

1,2-DICHLORO-1,2,2-TRIMETHYL-1-PHENYL-DISILANE AND METHOD FOR PRODUCING THE SAME

BACKGROUND OF THE INVENTION (i) Field of the Invention

This invention relates to 1,2-dichloro-1,2,2-trimethyl-1-phenyldisilane which is a novel asymmetric functional disilane, and a method for producing the same.

(ii) Description of the Prior Art

Heretofore, there is no prior arts which show a method for selectively introducing an aryl group into a disilane structure such as 1,1,2-trichloro-1,2,2-trimethyldisilane, and 1,2-dichloro-1,2,2-trimethyl-1-phenyldisilane prepared by selectively substituting one chloro group of the position "1-" of 1,1,2-trichloro-1,2,2-trimethyldisilane with phenyl group is a novel compound which has not been described in any prior arts.

SUMMARY OF THE INVENTION

An object of the present invention is to provide a novel asymmetric functional disilane, i.e. 1,2-dichloro-1,2,2-trimethyl-1-phenyldisilane expressed by the chemical formula (II), $$Cl(CH_3)_2SiSi(CH_3)(C_6H_5)Cl$$

(hereinafter referred to as "Disilane II").

Another object of the present invention is to provide a method for producing 1,2-dichloro-1,2,2-trimethyl-1-phenyldisilane (Disilane II) by reacting phenyl lithium with 1,1,2-trichloro-1,2,2-trimethyl disilane expressed by the chemical formula (III), $$Cl(CH_3)_2SiSi(CH_3)Cl_2$$

(hereinafter referred to as "Disilane III").

Still other object of the present invention is to provide a method for producing 1,2-dichloro-1,2,2-trimethyl-1-phenyldisilane (Disilane II) by reacting 1,1,2-trichloro-1,2,2-trimethyldisilane (Disilane III) with phenyl magnesium halide expressed by the general formula (IV), $C_6H_5MgX$ (X=halogen atom) (hereinafter referred to as "Grignard reagent") in the presence of a cobalt catalyst.

DETAILED DESCRIPTION OF THE INVENTION

Disilane II of the present invention is a compound useful as an intermediate for polysilane having various functions as an electroconductor, photoresist, optical information recording material or the like.

There is a proposal for preparing Disilane II by the reaction of Disilane III with phenyl magnesium halide such as phenyl magnesium iodide, phenyl magnesium bromide, phenyl magnesium chloride and the like. However, if this reaction is carried out in the absence of a catalyst, in addition to the desired 1,2-dichlorodisilane type Disilane II, 1,1-dichlorodisilane type 1,1-dichloro-1,2,2-trimethyl-2-phenyldisilane expressed by the chemical formula (I), $(C_6H_5)(CH_3)_2SiSi(CH_3)Cl_2$ (hereinafter referred to as "Disilane I") is also produced. Disilane II and Disilane I are produced in a ratio of about 1:1. Thus, this method has a disadvantage that Disilane I or Disilane II can not be produced selectively.

We have studied a method for selectively producing Disilane II alone from Disilane III, and have found that Disilane II alone can be selectively produced at a favourable yield by reacting Disilane III with phenyl lithium. The present invention is based on this finding.

The production step of Disilane II of the present invention can be illustrated by the following chemical reaction formula.

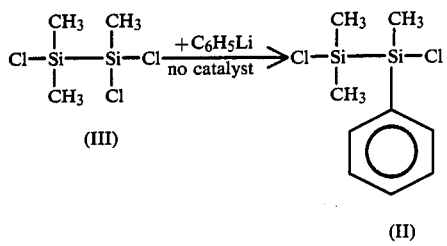

Disilane III used as the starting material in the present invention can be obtained by a disilane fraction by-produced when producing dichlorodimethyl silane from methyl chloride and metallic silicon.

Disilane II of the present invention can be prepared by reacting 1 equivalent of Disilane III with 0.9 to 1.1 equivalent of phenyl lithium in an aprotic solvent such as n-hexane, tetrahydrofuran, diethyl ether, toluene, benzene or the like. The preferable reaction temperature is 0° to 50° C., and the reaction is generally completed in 1 to 12 hours. However, the reaction of the present invention is not limited to these reaction conditions. After the reaction, the product is purified by normal purification method. Thus, the desired Disilane II of a high purity can be obtained at a high yield of 90% or more on the basis of Disilane III.

We have further studied a method for selectively producing Disilane II alone from Disilane III, and have found that Disilane II alone can be selectively produced at a favourable yield by reacting Disilane III with a Grignard reagent in the presence of a cobalt caytalyst. The present invention is based on this finding.

The production step of Disilane II in accordance with the present invention can be illustrated by the following chemical reaction formula.

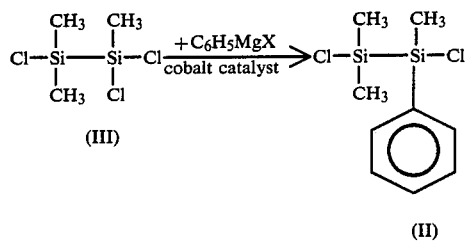

A typical example of a cobalt catalyst used in the present invention is cobalt chloride ($CoCl_2$), but should not be limited thereto.

Examples of a Grignard reagent used in the present invention include phenyl magnesium halide such as phenyl magnesium iodide, phenyl magnesium bromide, phenyl magnesium chloride and the like.

According to this invention, 1 equivalent of Disilane III is reacted with 0.9 to 1.1 equivalent of a Grignard reagent in the presence of 0.01 to 0.1 equivalent of a cobalt catalyst in an aprotic solvent such as n-hexane, tetrahydrofuran, diethyl ether, toluene, benzene or the like. The preferable reaction temperature is 0° to 50° C., and the reaction is generally completed in 1 to 12 hours.

However, the reaction is not limited to these reaction conditions. After the reaction, the product is purified by normal purification method. Thus, Disilane II of a high purity can be obtained at a high yield of 80% or more.

The present invention selectively provides 1,2-dichlorodisilane type Disilane II alone at a favourable yield by the reaction of Disilane III with phenyl lithium or the reaction of Disilane III with a Grignard reagent in the presence of a cobalt catalyst.

Disilane III used as the starting material in the present invention can be obtained by a disilane fraction by-produced at a yield of 10 to 20% when producing dichlorodimethyl silane from methyl chloride and metallic silicon. The disilane fraction thus by-produced is at present disposed or stored without being utilized. Thus, the present invention effectively utilizes unused resourses.

The present invention is further illustrated by the following Examples and Comparative Example.

COMPARATIVE EXAMPLE 1,1,2-trichloro-1,2,2-trimethyldisilane 103.8 g (0.5mole) and diethyl ether 200 g were placed in a one liter four-necked flask equipped with a condenser, dropping funnel, thermometer and stirrer, and a diethyl ether solution of phenyl magnesium bromide 90.5 g (0.5 mole) was dropwise added thereto for 3 hours while stirring at the reaction temperature of 25° to 30° C. After the dropwise addition, the stirring was continued for 2 hours at 25° to 30° C. to complete the reaction. In order to identify the reaction product, a small amount of the product obtained by separating the by-produced magnesium salt by filtration was reduced with lithium aluminum hydride and the reduced product was subjected to $^1$H-NMR spectrum ($C_6D_6$) analysis. At this result, hydrogens marked (a) and (b) as illustrated by the following chemical formulas could be indentified, and the intensity ratio of them was 1:1.

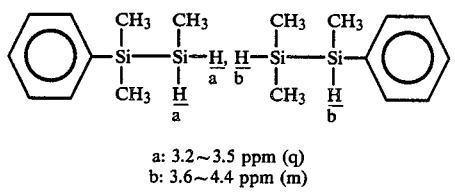

a: 3.2~3.5 ppm (q)
b: 3.6~4.4 ppm (m)

Thus, the reaction product this Comparative Example was proved to be a mixture of 1,1-dichloro-1,2,2-trimethyl-2-phenyldisilane and 1,2-dichloro-1,2,2-trimethyl-1-phenyldisilane in a ratio of 1:1.

EXAMPLE 1

1,1,2-trichloro-1,2,2-trimethyl disilane 103.8 g (0.5 mole), cobalt chloride 6.5 g (0.05 mole) and diethyl ether 200 g were placed in the same type of reaction apparatus as used in the above Comparative Example, and a diethyl ether solution of phenyl magnesium bromide 90.5 g (0.5 mole) was dropwise added thereto for 3 hours while stirring at the reaction temperature of 25° to 30° C. After the dropwise addition, the stirring was continued for 2 hours at 25° to 30° C. to complete the reaction. In order to identify the reaction product, the product obtained by separating the by-produced magnesium salt by filtration was subjected to $^1$H-NMR spectrum ($C_6D_6$) analysis in the same manner as in the above Comparative Example. As this result, it was proved that 1,2-dichloro-1,2,2-trimethyl-1-phenyl disilane could be produced at a favourable selectivity. The reaction product was then purified by a normal purification method to obtain 1,2-dichloro-1,2,2-trimethyl-1-phenyl disilane 103.5 g at the yield of 83%.

The various properties of the reaction product thus obtained were as follows:
Boiling Point: 129°–131° C./20 mmHg
Mass Spectrum: 249 (M+1)
Proton NMR Spectrum ($CCl_4$):

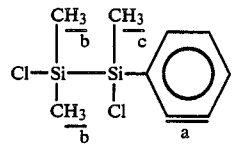

a: 7.1~7.6 ppm (m, 5H)
b: 0.45 ppm (s, 6H)
c: 0.65 ppm (s, 3H)

Infrared Absorption Spectrum (NaCl): (cm$^{-1}$) 3180, 2975, 1485, 1430, 1400, 1255, 1115.

EXAMPLE 2

1,1,2-trichloro-1,2,2-trimethyl disilane 103.8 g (0.5 mole) and petroleum ether 200 g were placed in the same type of reaction apparatus as used in the above Comparative Example, and an petroleum ether solution of phenyl lithium 42.5 g (0.5 mole) was dropwise added thereto for 3 hours while stirring at the reaction temperature of 25° to 30° C. After the dropwise addition, the stirring was continued for 2 hours at 25° to 30° C. to complete the reaction. In order to identify the reaction product, the product obtained by separating the by-produced lithium salt by filtration was subjected to $^1$H-NMR spectrum ($C_6D_6$) analysis in the same manner as in the above Comparative Example. As this result, it was proved that 1,1-dichloro-1,2,2-trimethyl-2-phenyl disilane was not substantially produced and that 1,2-dichloro-1,2,2-trimethyl-1-phenyl disilane could be produced at a favourable selectivity. The reaction product was then purified by a normal purification method to obtain 1,2-dichloro-1,2,2-trimethyl-1-phenyldisilane 113.4 g at the yield of 91%.

The various properties of the reaction product thus obtained were as follows:
Boiling Point: 129°–131° C./20 mmHg
Mass Spectrum: 249 (M−1)
Proton NMR Spectrum ($CCl_4$):

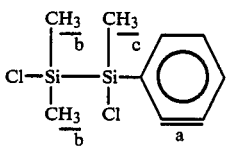

a: 7.1~7.6 ppm (m, 5H)
b: 0.45 ppm (s, 6H)
c: 0.65 ppm (s, 3H)

Infrared Absorption Spectrum (NaCl): (cm$^{-1}$) 3180, 2975, 1485, 1430, 1400, 1255, 1115.

What we claim is:
1. 1,2-dichloro-1,2,2-trimethyl-1-phenyldisilane expressed by the chemical formula (II),

$Cl(CH_3)_2SiSi(CH_3)(C_6H_5)Cl.$

2. A method for producing 1,2-dichloro-1,2,2-trimethyl-1-phenyldisilane by reacting phenyl lithium with 1,1,2-trichloro-1,2,2-trimethyldisilane expressed by the chemical formula (III), $Cl(CH_3)_2SiSi(CH_3)Cl_2$.

3. A method as claimed in claim 2, wherein one equivalent of said 1,1,2-trichloro-1,2,2-trimethyl disilane is reacted with 0.9 to 1.1 equivalent of said phenyl lithium in an aprotic solvent at a temperature of 0° to 50° C. for 1 to 12 hours.

4. A method as claimed in claim 3, wherein said aprotic solvent is selected from the group consisting of n-hexane, tetrahydrofuran, diethyl ether, toluene and benzene.

5. A method for producing 1,2-dichloro-1,2,2-trimethyl-1-phenyl disilane by reacting 1,1,2-trichloro-1,2,2-trimethyldisilane with phenyl magnesium halide expressed by the general formula (IV), $C_6H_5MgX$ (X=halogen atom) in the presence of a cobalt catalyst.

6. A method as claimed in claim 5, wherein said cobalt catalyst is cobalt chloride ($CoCl_2$).

7. A method as claimed in claim 5, wherein said phenyl magnesium halide is selected from the group consisting of phenyl magnesium iodide, phenyl magnesium bromide and phenyl magnesium chloride.

8. A method as claimed in claim 5, wherein one equivalent of said 1,1,2-trichloro-1,2,2-trimethyl disilane is reacted with 0.9 to 1.1 equivalent of phenyl magnesium halide in the presence of 0.01 to 0.1 equivalent of a cobalt catalyst in an aprotic solvent at a temperature of 0° to 50° C. for 1 to 12 hours.

9. A method as claimed in claim 8, wherein said aprotic solvent is selected from the group consisting of n-hexane, tetrahydrofuran, ethyl ether, toluene and benzene.

10. A method as claimed in claim 8, wherein said cobalt catalyst is cobalt chloride ($CoCl_2$).

11. A method as claimed in claim 8, wherein said phenyl magnesium halide is selected from the group consisting of phenyl magnesium iodide, phenyl magnesium bromide and phenyl magnesium chloride.

* * * * *